United States Patent [19]

Coggin, Jr. et al.

[11] Patent Number: 4,686,180

[45] Date of Patent: Aug. 11, 1987

[54] ONCO-FETAL SPECIFIC MONOCLONAL ANTIBODIES, METHODS OF PREPARATION AND USE

[75] Inventors: Joseph H. Coggin, Jr., Mobile, Ala.; William J. Payne, Jr., Indianapolis, Ind.

[73] Assignee: South Alabama Medical Science Foundation, Mobile, Ala.

[21] Appl. No.: 673,794

[22] Filed: Nov. 21, 1984

[51] Int. Cl.$^4$ .................. G01N 33/53; G01N 33/574
[52] U.S. Cl. .................. 435/7; 435/172.2; 435/948; 435/240.47; 436/513; 436/548; 436/804; 436/813; 530/387; 935/103; 935/104; 935/110
[58] Field of Search ............. 435/7, 172.2, 240, 948; 436/513, 518, 548, 804, 813; 935/110, 103, 104

[56] References Cited

U.S. PATENT DOCUMENTS 4,272,504  6/1981  Kim et al.
4,349,528  9/1982  Koprowski ............ 436/548 X

OTHER PUBLICATIONS

G. Kohler et al., Nature, 256 (5517), 495–497 (Aug. 7, 1975).
M. Votila et al., J. Immunol. Methods, 42(1), 11–15 (1981).
Shevinsky, L. et al., CELL, 30:697 (1982).
Sato, M. et al., Development, Growth and Differentiation, 25:333 (1983).
Coggin, Jr., J. H. et al., in Fetal Antigens and Cancer, Pittman, London (CIBA Foundation Symposium 96), p. 28 (1983).
Evans, D. et al., Cancer Research, 39:2006 (1979).
Coggin, Jr., J. H. et al., Journal of Immunology, 107:526 (1971).
Hanna, Jr., M. G. et al., Proc. Nat. Acad. Sci. USA, 68:1748 (1971).
Ting, C. C. et al., In Vitro, 14:207 (1978).
Weppner, W. A. et al., Cancer Research, 40:1380 (1980).
Coggin, Jr., J. H., Cancer Research, 39:2952 (1979).
Coggin, Jr., J. H. et al., Journal of Immunology, 105:524 (1970).
Gupta, R. K. et al., Journal of the National Cancer Institute, 70:993 (1983).
Kennett, R. H. et al., Science, 203:1120 (1979).
Pasternak, G. et al., Journal of the National Cancer Institute, 69:997 (1982).

*Primary Examiner*—Sidney Marantz
*Attorney, Agent, or Firm*—Saidman, Sterne, Kessler & Goldstein

[57] ABSTRACT

A process of preparing a hybridoma secreting oncofetal-specific monoclonal antibodies, which comprises: (a) immunizing an animal with immunizing amounts of a non-proliferating syngeneic mid-gestation fetal cell preparation; (b) isolating immunized animal lymphocytes; and (c) fusing the lymphocytes under appropriate fusion conditions with an immortalizing cell line to thereby obtain the hybridoma.

39 Claims, 6 Drawing Figures

ONCO-FETAL SPECIFIC MONOCLONAL ANTIBODIES, METHODS OF PREPARATION AND USE

The present invention was partly made using funds from the United States Government. The Government has certain rights in this invention.

BACKGROUND OF THE INVENTION

1. Field of the Invention

The present invention relates to onco-fetal antigens, monoclonal antibodies which are immunoreactive therewith, methods of preparation of these antibodies, and uses therefor, such as, for example, in cancer diagnosis and tumor typing.

2. Description of the Background Art

Cancer is one of humanity's most frightening and frustrating disease states. It is clear that the increased longevity of civilized man has greatly increased the probability that an individual will be afflicted with cancer. Cancer biologists are increasingly frustrated because most of the therapies available for the control of cancer, once it is clinically manifested, are at best palliative for the major killer forms thereof. Survival indexes have generally not improved among the major cancers that afflict man in spite of the billions of dollars in research and the millions of man-hours expended to develop new methods for cancer control. It is natural then that oncologists and tumor biologists have been desperately searching for better tools to detect cancer and to improve therapy based on a better understanding of cancer biology.

A small but significant number of spontaneous remissions that occur in otherwise untreatable tumors has encouraged biologists to hope that the body's natural defense mechanisms might be employed to better resist established tumors. This optimism has extended to the long range plan that someday it may even be possible, at least theoretically, to immunize humans so that cancers never appear.

In the past 20 years, cancer biologists have become aware that, for many human and experimental tumors of animals, the cancer host's immune system does seem to have memory for the antigenic determinants that are present in a wide variety of natural and artificially induced tumors. Alternatively, interference is detected against the immune responses (e.g., suppression). The precise description of the means by which this immunologic memory comes into play in the hosts' susceptibility to antigenic tumor growth, however, has only recently begun to be elucidated.

For many years, cancer biologists have concerned themselves with detecting and characterizing new antigens which appear in or at the surface of tumor cells. Many such determinants occur on virally and chemically-induced tumors of animals. The types of antigens which appear in or on transformed cells as a result of abortive infection with oncogenic DNA-containing viruses, like SV40 virus, or infection with the RNA-containing retroviruses, can generally be shown to occur on different species of cells transformed by each of these viruses; however, each virus species induces unique antigens to those induced by different tumor viruses. Chemically induced neoplasms are often antigenic in their host, but may lack the viral associated transplantation antigens.

Best known among the tumor associated antigens which appear during the course of, or following, viral transformation of cells either in vitro or in vivo are (1) tumor associated cell surface antigens; (2) membrane associated tumor specific or tumor associated transplantation antigens; (3) intracellular antigens located primarily in the nucleus, termed tumor or T antigens, which may only function as an immunogen when the tumors become large and necrosis occurs; (4) virus associated antigens present on virus particles or on maturing virus in the cell membranes per se; and (5) embryonal or fetal antigens re-expressed at the cell surface and also in the extracellular fluid when SV40 transformed cells are cultured in vitro. The embryonal or fetal antigens can be detected with antibody and also by transplantation rejection tests. (This introduction is essentially taken from Coggin, Jr. and Ambrose, *Methods in Cancer Research, Vol.* 18, Chap. 10, pp. 371-389.)

There have been many attempts to develop antibodies, both polyclonal or monoclonal, against tumor antigens in the hope of preparing diagnostic and therapeutic reagents. Two types of immunizations have been carried out in the prior art with this hope in mind: xenogeneic and allogeneic immunizations. Xenogeneic immunization is the immunization of an animal, such as a mouse or rat, with tissue (e.g., tumor tissue) of an animal from a different species (e.g., human). Allogeneic immunization is obtained by immunizing an animal from a given species with tissue derived from an animal of the same species but of a different strain. Xenogeneic immunizations of mice which provide monoclonal antibodies against human neuroblastomas, for example, are described in Kennett, R. H., Chaapter 10 of *Monoclonal Antibodies. Hybridomas: A New Dimension In Biological Analysis,* pp. 115-168. Monoclonal antibodies raised xenogeneically against human leukemic cells derived from mouse splenocytes are described, for example, in Sato, et al., *Development, Growth and Differentiation,* 25:333-344 (1983).

There are several problems associated with antibodies (whether polyclonal or monoclonal) prepared by xenogeneic immunizations. Perhaps the most important one is the obvious difficulty of ever establishing absolute tumor specificity of such antibodies. Few monoclonal antibodies derived by xenogeneic immunization of mice or rats with a given human tumor tissue have demonstrated absolute specificity for that tumor class and many react with some normal adult human tissue (See, for example, Rosenberg, S. A., in Rosenberg Ed., *Serological Analysis of Human Cancer Antigens,* New York, Academic Press, 1980). These problems are derived from the fact that human tumor cells contain not only tumor specific antigens, but also a host of other normal, non-tumor related antigens when injected into histoincompatible hosts. Thus, polyclonal sera raised against tumor cells of a different species or strain is, by necessity, immunoreactive with both tumor specific and tumor nonspecific antigens. The possibility of obtaining monoclonal (Mc) antibodies against specific epitopes has raised the hope that some of the Mc's, randomly selected from hybridoma supernatants, would be truly tumor specific. This, however, is a tedious and laborious process, and provides poor guarantee of reproducibility of results. The results are "hit or miss" and are based on classic immunologic approaches for "raising" antibodies.

Over the last 10-15 years, there has developed, along a different line of cancer research, the possibility that the majority of malignant tumors of humans and rodents carry common embryonic determinants (EA) which can be immunogenic in the syngeneic host and are associated with the cell plasma membrane (See, for example, Coggin, Jr., *Fetal Antigens and Cancer*, Pittman, London (CIBA Foundation Symposium 96), pp. 28–54 (1983)). By the definition used herein, true EAs are uniquely expressed on germinal, embryonic and some fetal cell membranes, and are not expressed (immunogenic) in normal adult tissues nor in regenerating tissues. The immunological role of embryonic antigens in fetal development in utero is still obscure. It is known that maternal antibodies are produced in response to EA's expressed in utero. The biological product of the oncogenic process that leads to the re-expression of EA in the emerging malignant cell clone seems to be intimately associated with the promotion of tumor protected immune responses in the host. These responses mimic immune responses in pregnancy, which may serve to protect the EA+ fetus from maternal immune attack.

Embryonic antigens are indeed expressed by all classes of tumors of rodent and man. Some fetal antigen equivalent—onco-fetal antigens or OFA's—expressed in human tumors (for example, melanomas) appear to be segregated among distinct histologic classes, although common EA's have also been reported. It has been shown (Ambrose, K. R., et al., *Nature* 233:194 (1971); Coggin, J., et al., *Advanced in Cancer Research* 19:105 (1974) and Coggin, *CIBA Symposium*, supra) that rodent and human embryonic antigens shared as common immunogenic determinants and conserved in the evolution of species, are re-expressed as OFAs on human as well as rodent tumors. This idea originally arose from the observation that irradiated human fetal kidney cells as well as syngeneic irradiated hamster fetal cells could interrupt SV40 oncogenesis in hamsters. Adult human tissues were not similarly protective. This implies that rodent embryonic antigens are related to rodent onco-fetal antigens, and that rodent embryonic antigens are identical with some human embryonic antigens. Since embryonic antigens present on human fetal kidney cells elicited protection against SV40-activated hamster embryonic antigens, at least some human embryonic antigens are equivalent to rodent oncofetal antigens.

Until recently, the nature of EAs was obscure since no reagents were available to immunochemically characterize them. A number of workers, however, have reported the detection of a variety of purported fetal antigens though none have been purified with monoclonal antibodies. Price, M. R., *Soc. Trans.*, 2:650 (1974), detected a large uncharacterized fetal associated antigen with an estimated molecular weight of 100 kD in rat hepatomas. Evans et al., *Can. Res.*, 39:2006 (1979), found that sarcomas of rats exhibited two onco-fetal antigens estimated to fall in the range of 3.5 and 10 kD. Dickinson et al., *Br. J. Cancer*, 29:425 (1974), reported that human tumor extracts of breast, cervix, vagina and omentum contained several small common proteins that appeared to be fetal associated, ranging in size from 16–18 kD. Jornvall et al., *P.N.A.S.* USA 79:287 (1982), reported the detection of a 53 kD onco-fetal protein which has been sequenced and found to share DNA binding properties with polyoma middle T antigen (55 kD). This transformation-associated protein was present in mid-gestation fetal cells in several species as well as in several human and adult tumor types evaluated.

While performing studies on the occurrence of rodent and/or human embryonic antigens on human tumor cells, some investigators have carried out syngeneic immunizations. A syngeneic immunization is one derived in an animal system devoid, by immunological methods, of detectable histo-incompatibility determinants. In other words, syngeneic immunizations are those obtained from immunizing a given animal with tissue from a genetically identical animal (i.e., some species, same strain).

Coggin, Jr., et al., *The Journal of Immunology* 105:524 (1970) and Coggin, et al., *Adv. Can. Res.*, 19:105–165 (1974), showed that hamster and mouse fetal cells contained antigens cross-reactive with an SV40-induced sarcoma and on other viral and chemically-induced sarcomas, in that they stimulated an antibody. The antibody was synthesized when 10 day, but not 14 day, irradiated hamster fetal cells were injected into adult syngeneic hamsters, and these animals were subsequently found to exhibit immunity to SV40 tumor cell challenge. Non-irradiated fetal cells failed to induce transplantation immunity.

Hanna, Jr., Coggin, et al., *Proceedings of the National Academy of Sciences, U.S.A.* 68:1748 (1971), studied the suppressive effects of immunization with mouse fetal antigens on growth of cells infected with RLV virus and on plasma cell tumors. Young BALB/c male mice were primed at three week intervals with x-irradiated syngeneic embryo cells. The development of tumors was suppressed in the mice. Similar expressions were not observed in mice primed with neonatal or normal xenogeneic cells.

Ting, *In Vitro* 14:207 (1978), following the work described by Coggin, Jr. et al. (supra) employing sensitization to syngeneic fetus in hamsters and Balb/c mice, studied the expression of fetal antigens derived from mouse fetal cells. Antisera were produced by syngeneic immunization with 5,000 R x-irradiated tissues from mouse fetuses of one to two weeks gestation period. Fetal antigens were found to be retained even after five years in in vitro transformed cell lines from actual mouse fetal tissues.

All of these studies using syngeneic immunizations were carried out for the purpose of analyzing the presence of embryonic antigen on cells and their induction of immunity against tumors in the host. No production of hybridomas and Mc antibodies to fetal specific determinants on fetal tissues from a syngeneic host, has been described. Derivation of monoclonal antibodies reactive against any of the embryonic antigen determinants on the surface of hamster or mouse fetal cells of known gestational age has been expected to be problematic at best since such efforts would involve immunization within syngeneic systems. An additional complication would be that the usual course of multiple immunizations commonly reported in the monoclonal literature with soluble, crude embryonic antigen preparations have already been shown to activate T-suppressor lymphocytes, and to interfere with tumor transplantation immunity in a dose-dependent fashion (Weppner, W. A., et al., *Cancer Research* 40:1380 (1980)). The effects of hyperimmunization with syngeneic fetus on B lymphocyte activation were also unknown prior to this invention. Female rodents have been observed to develop cytostatic IgG to embryonic antigens cross-reactive with SV40 sarcoma cells when immunized directly with irradiated, syngeneic fetal cell preparations containing many disrupted fetal cells, but did not develop tumor resistance and presumably cytotoxic effector T cells under such conditions (Ambrose, K. R., supra; Coggin, J. H., *Cancer Reserach*, 39:2952 (1979).

Indeed, Shevinsky et al., *Cell*, 30:697–705 (1982), reported great difficulty in obtaining hybridomas with embryo-sensitized mouse or rat spleens. Only one embryo-specific monoclonal antibody (out of 2,000 clones in 14 fusions) could be obtained and reported. This, moreover, was obtained by xenogeneic immunization.

Thus, there were, prior to the present invention, several reasons in the art for expecting that syngeneic immunization might not work or even prove immunogenic to produce lymphocytes useful in the formation of hybridomas and of monoclonal antibodies applicable in diagnosis and/or therapy.

Because of the great need for obtaining immune reagents capable of high specificity with regard to detecting conserved EAs or OFAs in human tumors, the prior art prejudices were nevertheless ignored when the initial studies leading to the present invention were carried out.

SUMMARY OF THE INVENTION

The present invention arose out of the unexpected discovery that it is possible to carry out syngeneic immunization of an animal with non-proliferating (e.g. lethally irradiated) mid-gestational syngeneic fetal cells to produce lymphocytes, and eventually monoclonal antibodies highly specific for embryonic antigens on rodent and man. Spleen cells obtained from mice sensitized in this manner can be fused with appropriate immortalizing cells under known conditions to produce hybrid myelomas (hybridomas) which, after selection, screening and cloning, are found to produce monoclonal antibodies which are highly specific to the embryonic antigens. These monoclonal antibodies have the special property of cross-detecting human onco-fetal antigens which appear to be identical or nearly so to rodent and human EAs. The monoclonal antibodies obtained by such process are capable of specifically detecting a unique oncofetal polypeptide determinants heretofore not described in the published literature.

The invention thus comprises a process of preparing hybridomas and monoclonal antibodies by the steps of:
(a) immunizing an appropriate animal with suitable amounts of a syngeneic, non-proliferating, mid-gestation fetal cell preparation;
(b) isolating sensitized lymphocytes from said animal;
(c) fusing said lymphocytes under appropriate fusion conditions with an immortalizing cell line to thereby obtain a hybridoma; and
(d) obtaining monoclonal antibodies from said hybridoma.

One of the critical aspects of the process is the syngeneic immunization of animals with non-proliferating fetal cells. The ability to obtain the results of the invention goes against the prior art belief and prejudice that embryonic antigens would be difficult to use as immunogens because they are generally believed to be non- or poorly immunogenic in vivo in Balb/c mice, hamsters and were immunosuppressive when given over prolonged immunization schedules using cell free crude antigen preparations, and that they were strictly phase specific, prohibiting their culture in vitro. Further, the process confirms that it is possible to develop Mc Igs to evolutionarily conserved embryonic antigens which are widely expressed on rodent and human tumors.

The invention also relates to the type of monoclonal antibodies obtained by the process, specifically to monoclonal antibodies which have the following specificity characteristics:
(a) immunoreactivity towards rodent and human mid-gestation embryonic-fetal antigens;
(b) immunoreactivity towards human oncofetal tumor antigens;
(c) substantially no detectable immunoreactivity towards rodent late gestational fetal tissue or adult tissues of mouse, hamster or man; and
(d) substantially no detectable immunoreactivity towards human normal tissue.

The antibodies can be used to isolate tumor associated antigens by affinity chromatography; to identify tumors expressing OFAs by diagnosis, detection of primary tumors, as well as metastasis or tumor typing; to provide for the specific delivery of reagents or bound cytotoxic drugs to tumor cells; and to provide potential passive immunity by cytotoxic killing of tumor cells.

The invention also relates to certain novel oncofetal antigens useable as diagnostic and/or typing markers for tumors, one of which is a polypeptide having an approximate molecular weight of 44,000–48,000, and another is a polypeptide (which may be a covalently-linked multimer of the first one), having an approximate molecular weight of 200,000.

The present invention opens the way to a class of truly onco-fetal specific reagents.

+++=full color in 10 min; ++=color in 15 min; +=some color in 20 min; o=no color.)

Figure 5:
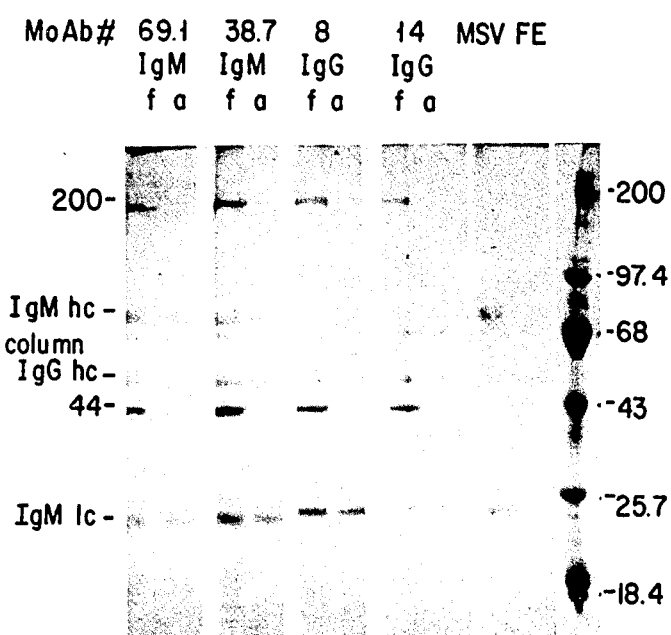

FIG. 5 shows the detection of fetal specific 44–46 kD and 200 kD polypeptides in NP40 extracts (4 ugs) of 12 dmfcs or adult mouse tissues loaded to the Sepharose 4B:Mc antibodies listed. The gel complex was washed thoroughly, eluted, and the eluate prepared for SDS-PAGE electrophoresis and stained with Coomassie blue. A mouse Mc IgM to Moloney sarcoma virus envelope glycoprotein determinant (MSV) was used as a control Mc with the fetal cell extracts. f=fetal extract; a=adult tissue extract. Right most lane shows standard mol. wt. markers. 19–20 day mouse fetal cells gave identical results shown above for adult cells.

Figure 6:
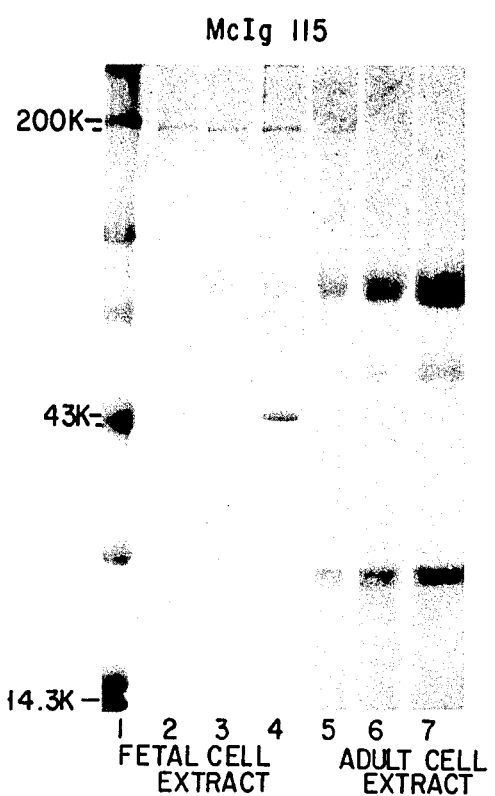

FIG. 6 shows the capacity of Mc115 shIII to remove increasing amounts of the fetal specific 44 and 200 kD polypeptides from NP40 extracts of 12 day mouse fetal cells. Lane 1=molecular wt. standards; Lane 2=Mc 115 shIII+10 ul of fetal extract; Lane 3=Mc 115 shIII+20 ul of extract; Lane 4=Mc 115 shIII+30 ul of extract; Lane 5=Mc 115 shIII+10 ul of 10x adult extract; Lane 6=20 ul of extract; Lane 7=30 ul of extract.

BRIEF DESCRIPTION OF THE PREFERRED EMBODIMENTS

Processes

The invention is based on carrying out syngeneic immunization of animals with a non-proliferating, mid-gestational fetal cell preparation. Any appropriate animal can be utilized such as, for example, rodents, such as mice, rats or hamsters; goats; horses; chickens; and the like. Most preferred are mice. Indeed, after extensive experimentation, it was discovered that a well characterized, inbred strain of mice, well-known to those of skill in the art and available commercially, C57BL/6n, was the very best in order to obtain the final hybridomas. Another inbred strain of Balb/c mice could not readily be used in initial trials.

It is crucial that the syngeneic fetal cells be mid-gestational for the gestational period of the chosen species, and obtained from primaparous females. Thus, for example, mid-gestation for the mouse is between 12 and 14 days, whereas for the hamster it is 9–10 days. The reason for this requirement is that embryonic antigens are phase specific. Early stages of gestation are likely antigen positive but the amount of fetal tissue is very small and these early period tissues are not useful. If normal adult cells, term fetal cells (19–21 days mouse or 15 day hamster) or neonate cells or adult mouse or hamster tissues are used, successful results cannot be obtained.

Another condition for successful immunization is the need to arrest proliferation in the syngeneic immunizing fetal cell preparation. The arresting of proliferation can be carried out by any of a number of well-known processes of stopping DNA replication such as, for example, irradiation with x-rays, ultraviolet or cesium radiation, or iododeoxyuridine treatment. Preferred is x-ray irradiation at about 4,000–6,000 R in whole cells, prior to immunization. If continuous cell replication is allowed during immunization, the embryonic antigens disappear from the cell surface rapidly (as immunogens) and obtainment of the desired hybridomas is not successful.

Harvesting and dispersing of fetal cells (prior to immunization) has been described in Coggin, J. H., et al., *Advances in Cancer Research*, 19:105 (1974)). Enzyme dispersal is preferably not used.

It is noteworthy that many initial immunization attempts using pregnant donors, Balb/c donors injected with fetal cells and high dose, long course sensitization, conventionally used to produce hybridomas, were not successful. Best immunization is by cells ideally given in either a short term course of three injections total including final boosting. Cells can be injected by themselves or in Freund's adjuvant with either *Mycobaterium smegmatitis* or *M. tuberculosis* followed by a booster injection with fetal cells and incomplete Freund's, and a final boost with fetal cells only. Injections can be intraperitoneal or intravenous, the former being most suitable. Sensitized spleen cells can be obtained about three days following the final boost, which is usually given about 2–3 weeks after the last immunogen injection. Immunizing amounts of fetal cells are normally anywhere between $10^6$ and $10^8$ per injection. Whole cells or carefully prepared cell membranes or other EA-containing cell-extract preparations can be used, but in such case the immunizing regimen must be rigorously controlled to restrict the development of supressor cells (Weppner & Coggin, *Cell Imm.*, 54:193, 1980).

After obtaining sensitized spleen cells, the same are fused under appropriate fusion conditions with any desired immortalizing cell line, to give hybridomas. The processes for preparing hybridomas and selecting the same as well described in *Monoclonal Antibodies. Hybridomas: A New Dimension in Biological Analysis*, edited by Kennett, McKearn and Bechtol, Plenum Press, New York and London (1982), especially the Appendix entitled "Methods of Reproduction and Characterization of Monoclonal Antibodies," at pp. 363–417, herein incorporated by reference in its entirety. One of the preferred immortalizing cell lines is P3X63Ag8.653. The fusion may be carried out at a 1:10 cell ratio of murine myeloma cells to spleen cells in the presence of polyethylene glycol. Selection is normally carried out in a selective medium such as, for example, HAT. Hybrid cells are maintained in HT medium, supplemented with the supernatants from the macrophage cell line RAW264.7. This medium is essential to obtain vigorously growing IgM-producing hybridomas. This macrophage line has been deposited prior to the filing data of the present application at the American Type Culture Collection, and has been assigned No. CRL 8668.

Cloning of mass hybridoma colonies can be carried out by any of a variety of methods such as, for example, terminal dilution or colony formation in methyl cellulose. Immunoglobulin class can be defined by, for example, immunodiffusion assays and utilization of typing antibodies (anti-mouse immunoglobulins). It has been observed that, in all instances involved in the present invention, the monoclonal antibodies are of the IgM class when induced with intact fetal cells, and are IgG isotypes when induced with soluble fetal cells. This, however, should not be limiting, and other classes may be obtainable and usable.

A critical test of the specificity of the monoclonal antibodies with respect to embryonic antigens is carried out by absorption screening of colony supernatants with acetone powders prepared from newborn and adult mouse tissues (C57BL/6n or with whole tissue, freshly collected). A packed volume of acetone powder is mixed with an equal volume of hybridoma supernatant, and incubated. The mixture is centrifuged before use in an enzyme linked immuno absorption assay (ELISA). If the absorbed hybridoma supernatant gives a positive reaction, then it is considered to be against a true determinant and is processed for cloning.

PRODUCTS

The monoclonal antibodies obtainable by the aforementioned process have substantial immune reactivity towards mid-gestation embryonic-fetal antigens of the originating animal; have substantial immune reactivity towards human and rodent oncofetal tumor antigens; have substantially no detectable immune reactivity towards late gestational fetal tissue derived from the originating animal; and have substantially no detectable immune reactivity towards human normal tissue.

When the animal being immunized is a mouse, the monoclonal antibodies of the invention have immune reactivity towards rodent mid-gestation antigens, but no immune reactivity towards rodent late gestational tissue.

Since the embryonic antigens at mid-gestation reappear as oncofetal antigens in human cancer cells, but do not exist in detectable concentrations in human normal adult or neonate or term fetal cells, the monoclonal antibodies obtained are highly fetal and tumor specific. Indeed, since the mid-gestational syngeneic cells do not carry any antigens (other than the embryonic antigens) which differ from those of the immunizing host, the monoclonal antibodies derived therefrom are truly specific or EA's and for OFA's.

Of interest concerning the specificity of the monoclonal antibodies of the present invention is the observation by the inventors that polyclonal in vivo absorbed xenogeneic antiserum derived against 10 day gestation hamster fetal cells immunoprecipitates apparent fetal specific polypeptides from 3M KCl or NP-40 extracts of 12-13 mouse or 10 day hamster fetal cells. Such studies also indicate that some 10-12 polypeptides are present at this time in gestation and not present in neonatal or adult tissues; some of these may be polymeric forms of smaller polypeptides. Most embryonic antigens detected are common to both rodent (mouse and hamster) species. A spectrum of tumor lines known to share embryonic antigens with 10 day gestation hamster fetal cells are also killed by the polyclonal antiserum. On the other hand, certain tumor lines which do not share detectable oncofetal antigens with hamster fetal cells are not killed. Neither are adult human normal fibroblasts. The anti-EA IgG's present in the polyclonal serum specifically immunoprecipitate several embryonic antigen determinants, indicating that there are several but only a limited number of EA polypeptides recognized by the IgGs present.

These results obtained with polyclonal serum are consistent with the specificity of the monoclonals of the invention. The monoclonals of the invention have a narrow range of specificity.

In all instances, they recognize one unique polypeptide with approximate molecular weight 44,000-48,000 Daltons. They also recognize a polypeptide of approximate molecular weight 200,000 Daltons from the same fetal cells. The latter may be a multimer of the 46 kD polypeptide or may represent as a second polypeptide carrying the same EA epitope as is present on the 46 kD protein. The 46 kD polypeptide is an antigen unique for embryonic mid-gestation, and appears to be a true embryonic, and thus, oncofetal antigen.

METHODS OF USE

The monoclonal antibodies of the invention can be used in a wide variety of applications. These applications include diagnostic, therapeutic, analytical imaging, and research applications.

Among the diagnostic methodologies available, one aspect of the invention is drawn to a method of detecting an oncofetal antigen associated with a human tumor which comprises:

(a) incubating a human sample suspected of containing said oncofetal antigen with a monoclonal antibody according to the invention; and (b) determining if any substantial binding occurs between said antigen and said antibody.

The detection of the oncofetal antigen can be carried out by methods well known to those of skill in the art of immunoassay technology. For example, competitive assays or immunometric assays can be used. In a competitive assay, monoclonal antibody is incubated with a detectably labelled amount of oncofetal antigen and with specimens suspected of containing oncofetal antigen in an unknown quantity. Competition between the detectably labelled antigen and the antigen present in the specimen occurs, leading in a relatively straightforward manner, to a quantitation of the amount of antigen in the specimen.

In immunometric assays, monoclonal antibody according to the invention is (previously or in delayed phase) immobilized on an appropriate solid phase and incubated with a sample suspected of containing oncofetal antigen associated with a human tumor. The same or different monoclonal antibody, in soluble, detectably labelled form is then incubated with the sample and, after appropriate washing procedures, leads to formation of a complex, with concommitant binding of label to the solid phase. A straightforward proportional relationship between the label and the amount of oncofetal antigen present in the sample can be obtained. Immunometric assays can be carried out in the forward, reverse or simultaneous modes. These are all well known to those of skill in the art. See, for example U.S. Pat. No. 4,376,110 to David et al. drawn to "Immunometric Assays Using Monoclonal Antibodies." For immunometric assays specifically using IgM monoclonal antibodies against multivalent antigens, also see, for example, Wands, et al., PCT/US 81/01270.

Any detectable label can be utilized either on labelled antigen or labelled antibody. These labels include radiolabels (for example, $^{32}P$, $^{125}I$, $^{3}H$, $^{35}S$, $^{14}C$, and the like). They include enzymes to be used in ELISA techniques (for example, alkaline phosphase, horseradish peroxidase, penicillinase, and the like), fluorogenic compounds (such as fluorescein), bacteriophages, metals useful for NMR imaging techniques, other radiolabels useful in radioimaging techniques, and the like. Radiolabels or enzyme labels are preferred for assays.

Any appropriate and well known solid phase useful in immunoassays can be utilized. These include latex particles, polystyrene beads, test tubes, fibers, wells, other natural and/or synthetic polymeric materials, and the like.

Mc Ig purified antigens can be used for conventional skin testing for sensitization to the OFA and as antigens in lymphocyte transformation assays. The antigens may also be useful in sensitizing the host's immune system against tumor development or recurrence.

The embryonic antigens discovered in the invention can also be utilized as markers for the detection and/or diagnosis of tumors by the standard immunoassays described previously. These assays may use antibodies prepared by the process of the invention or other analogous antibodies equivalent thereto prepared by any other method. The assay may utilize the noted polypeptides in detectably labelled form (e.g. competitive mode), or in insolubilized form (agglutination assay for antibodies, or binding assay for antibodies). Thus, for example, the detectably labelled or immobilized polypeptides of MW 44,000-48,000 and having the embryonic antigen-OFA characteristics described herein are also part of the invention.

Complexes with monoclonal antibodies of the antigens comprising the polypeptides are also part of the invention. Such complexes occur, for example, when a monoclonal antibody binds to the polypeptide in a diagnostic assay in vitro, or in a diagnostic, imaging, or therapeutic procedure in vivo. Thus, complexes useful in radioimaging procedures (e.g. radioactive or nuclear magnetic resonance methods) wherein the monoclonal antibody is bound to a radioisotope or a metal atom or atoms are also part of the invention.

Additional uses include binding a monoclonal antibody according to the invention to a compound capable of suppressing, inhibiting or delaying tumor growth or propagation, and utilizing the conjugate as a selective "magic bullet" therapeutic reagent. Other therapeutic uses for the antibodies also include passive immune therapy.

Other applications for the antigens and/or antibodies include embryonic antigen detection on human fetus to ascertain normalcy of pregnancy; analysis of differentiation markers in fetal biology; purification of embryonic antigens and oncofetal antigens; human and animal tumor typing; screening for circulating oncofetal antigens in tumor patients; and analysis of tumor differentiation markers.

Tumor typing is of particular interest. There are four basic types of tumor classes: carcinomas, lymphomas, leukemias and sarcomas. Several subclasses exist within each. The oncofetal antigens may appear in different tissues. For example, certain oncofetal antigens may appear on colon carcinoma and different ones may appear on breast carcinoma. Thus, panels of monoclonal antibodies obtained according to the present invention can be prepared, whereby quick screening procedures can be carried out to ascertain not only the presence of a particular oncofetal antigen in an adult specimen, but also its classification as a carcinoma, lymphoma, leukemia or sarcoma, and further, the tissue source (colon, breast, etc.)

The present invention thus lends itself to the preparation of kits to carry out the noted applications. Such kits may comprise a carrier being compartmentalized to receive in close confinement therein one or more containers, wherein a first container may contain (for example) a monoclonal antibody according to the present invention in insoluble form, and a second container may contain the same or a different monoclonal antibody in soluble detectably labelled form. A user could then carry out an immunometric assay for a given oncofetal antigen. A series of containers containing varying concentrations of oncofetal antigen could be present in the kit so as to allow the preparation by the user of a standard calibration curve.

In addition, in order to allow for tumor typing, the kit may comprise a series of containers with predetermined different monoclonal antibodies in detectably labelled form or insoluble form, or both, so that quick screening and differential analysis can be carried out on a given human tumor sample (such as a biopsy, etc.).

Having now generally described this invention the same will be better understood by reference to certain specific examples which are included herein for purposes of illustration only and are not intended to be limiting unless otherwise specified.

EXAMPLE 1

In this example are described methods for the successful development of several monoclonal antibodies to mouse embryonic antigens, the establishment of a rapid screening system for the monoclonal antibodies using intact mouse fetal cells, definition of the isotype and illustration of specificity of the monoclonal antibodies for EA containing tissues and cells, and description of a solid phase ELISA method for quantitatively assessing monoclonal antibody titer to cell surface associated EA. The epitope is found to be expressed in human and hamster as well as mouse fetus, and on a spectrum of rodent tumors.

MATERIALS AND METHODS

Chemicals

Hanker/Yates, phenylhydrazine and dimethyl sulfoxide (DMSO) were commercially obtained.

Cells

The mouse macrophage cell line RAW 264.7 was grown in Dulbecco's medium with 10% fetal calf serum (CS), 2 mM L-glutamine and 0.045% sodium bicarbonate. The filtered culture medium from confluent cultures of these cells were used to supplement hybridoma growth medium. Mouse L cells were grown in Eagle's minimum essential medium with Earle's salts supplemented with 5% fetal bovine serum (FBS), 2 mM L-glutamine and 0.045% sodium bicarbonate. WF5-1 SV40-induced hamster (LVG) sarcoma cells and mKSA cells, an SV40 transformed mouse (Balb/c) sarcoma, were grown in 199 medium supplemented with 10% FBS, 2 mM glutamine and 0.045% sodium bicarbonate. GD-36, SV40 transformed hamster (LVG) lymphoma cells were maintained in RPMI 1640 with 10% FBS, 2 mM L-glutamine and 0.045% sodium bicarbonate.

Protocols for Immunization of C57BL/6n Mice for Use in Fusions for Hybrid Cells Attempts to elucidate the most productive immunization protocol for stimulation of the humoral response to fetal antigens in syngeneic male recipients were made by using seven separate groups of animals receiving concentrations of intact, syngeneic, 12 day gestation fetal cells of 3M KCl extracts thereof, at different modes of administration and/or time courses of injections. Harvesting and dispersing fetal cells for immunization was as described in Coggin it al., *Advanced Cancer Research* 19:105 (1974). Enzyme dispersal was never used. As shown in Table 1, groups of mice received either high ($10^7$) or low ($10^6$) concentrations of syngeneic, lethally-irradiated (5000 R), mid-gestation (10-12 day) mouse fetal cells.

TABLE 1

Immunization Groups[a] for Stimulating Immune Spleen Cells (C57Bl/6n) to Fetal Determinants (EAs)[b]

1. (SH) = Short term, high dose group. Two doses of $10^7$ viable 13 d C57BL/6n fetal cells administered intraperitoneally one week apart. Single boost of same dosage 3 weeks following last dose and 3 days prior to harvesting spleen cells for fusions.
2. (SL) = Short term, low dose group. Same as #1 except $10^6$ viable 13 d C57BL/6n fetal cells used.
3. (CFA Ms) = Complete Freund's adjuvant with *Mycobacterium smegmatitis* group. Single dose of the complete Freund's adjuvant and packed fetal cells mixed 1:1 (v/v) administered 0.03 ml to each hindfoot pad and 0.04 ml subcutaneous in midback. One week later, the inoculations were repeated using incomplete Freund's adjuvant. The final boost of cells only was given three weeks later.
4. (CFA Mt) = Complete Freund's adjuvant with *M. tuberculosis* group. Same as #3 but different Mycobacterium.
5. (LH) = Long term, high dose group. Same as SH group but 5 weekly doses given before final boost.
6. (LL) = Long term, low does group. Same as SL group but 5 weekly does given before final boost.
7. (3M KCl) = 3M KCl solubilized fetal cell group. Two doses of 3M KCl extract of 13 d C57BL/6n fetal cells delivered ip. with 700 μg protein and 450 μg protein respectively. Final boost of 100 μg protein given intravenously.

[a]Four (4) adult (5 week) male C57BL/6n mice per group.
[b]Fetal cells for immunizations were all 13 d syngeneic cells freshly prepared and receiving 5000 R x-ray prior to injections.

Cells were given in either a short term course of 3 injections total including final boosting, or a long term course of 6 injections total. Two other groups received fetal cells in Freund's adjuvant with either *Mycobacterium smegmatis* or *M. tuberculosis* following by a booster injection with fetal cells and incomplete Freund's and a final boost with fetal cells only. The adjuvants were mixed with equal volumes of packed cells, and 0.03 ml of the antigen preparation was given in both hind footpads and 0.04 ml was delivered subcutaneously on the back of each mouse. One group of mice was immunized with two intraperitoneal injections of 3M KCl solubilized fetal cell membranes at 0.5 mg protein per mouse followed by a final boost of 0.1 mg intravenously. All final boosts were given 2-3 weeks after the last immunogen injection. The sensitized spleen cells were obtained three days following the final boost.

Hybridoma Cultures

Hybridoma cells were made from fusions of the mouse myeloma, P3X63Ag8.653, and spleen cells from adult, male C57BL/6n mice immunized with lethally-irradiated mid-gestational syngeneic fetal cells. The fusions were performed by modifications of the method of Kohler and Milstein (*Nature* 256:495 (1975)) using a 1:10 cell ratio of murine myeloma cells to spleen cells in the presence of 50% (v/v) polyethylene glycol 4000. Hybrid cells were selected in RPMI 1640 medium containing hypoxanthine, aminopterin, thymidine, 15% FBS, 2 mM L-glutamine, 0.045% sodium bicarbonate and 50 ug/ml gentamicin (HAT medium). The cells were seeded in 96 well flat bottom Linbro plates at $3.5 \times 10^5$ cells per well. Hybrid cells were maintained, following transfer to 24 well Linbro plates, in RPMI 1640 medium supplemented with hypoxantine, thymidine, 15% FBS 2 mM L-glutamine, 0.045% sodium bicarbonate and gentamicin (HT medium). The transfer medium was also supplemented with 10% volume of filter sterilized 72 hr culture supernatants from the macrophage cell line, RAW 264.7 (HT+RS medium). Antibodies to fetal determinants present in the culture supernatants were measured when the hybrid cultures were fully adapted and could readily be passaged in vitro.

Cloning Mass Hybridoma Cultures for Mc Producing Hybridomas

Cloning of mass hybridoma colonies was performed by terminal dilution in HT medium supplemented with 10% RAW 264.7 culture supernatant. One hundred (100) and two hundred (200) hybridoma cells from a mass culture were suspended in 10 ml of the above cloning medium and dispensed into a 96 well plate with 100 ul of HAT+RS medium/well. Clones were then transferred to 24 well plates and mature colonies were later assayed for anti-EA activity. Recloning was performed on one or more occasions for each hybridoma.

Mc Immunoglobulin Class

A double immunodiffusion assay was used to elucidate the immunoglobulin class of the monoclonal antibody. Five ml of 1.5% agarose with 2.5% polyethylene glycol-4000 was melted in boiling $H_2O$ and subsequently equilibrated to 56° C. for 15 min. The agarose solution was then poured in an immunodiffusion plate (Miles Laboratory, Inc.) and allowed to solidify at 25° for 30 min. 5 mm wells were cut into the agarose in the configuration of a central well surrounded by 6 symmetrically spaced wells. 10 ul of the 25× concentrated monoclonal hybridoma supernatant was dispensed into the central well and 10 ul of six anti-mouse immunoglobulin sera, including: anti-$IgG_1$, anti-$IgG_2$, anti-$IgG_{2a}$, anti-$IgG_{2b}$, anti-$IgG_3$, and anti-IgM (Miles Laboratory, Inc.), was dispensed in the surrounding wells. The plates were incubated for 48 hours at 25° C. and observed daily for precipitin lines. Normal mouse serum and P3X63 Ag8.653 culture supernatant were used for a positive and negative control respectively.

Apparatus for Immunofiltration ELISA

The Reusable Microfold TM apparatus from V and P Scientific, Inc., San Diego, Calif., was used to perform the ELISA procedure. Glass fiber filter paper from V & P Scientific was used to trap and immobilize the target cells. The filter paper was pretreated with 2% gelatin that was melted off from under the wells by hot water (90° C.) prior to application of the cells.

Target Cells for Immunofiltration ELISA

The target cells used for the ELISA procedure were freshly harvested, primaparous, time-mated 12-13 day gestation C57BL/6n fetal cells. Whole, living fetuses were removed aseptically from the uterus and rinsed thoroughly 5× in Hank's balanced salts solution (HBSS), pH 7.0, before being expressed through a 20 gauge needle into fresh HBSS at 37° C. After gentle pipetting 2-3 times, the cells were filtered through a sterile 4×4 cotton gauze pad to remove debris. The cells were washed in HBSS by low speed centrifugation and then counted and $5 \times 10^6$ cells were resuspended in 10 ml of 0.05% phenylhydrazine in phosphate buffered saline (PBS), 10 mM, pH 7.4 and incubated for 30 min at 25° C. to inhibit endogenous peroxidase activity. The treated cells were then used directly in the ELISA.

Cultured tumor cell lines used in the filtration ELISA were suspended by scraping cells off flasks and dispersing by pipetting. The cells were then washed twice with HBSS before resuspension in the phenylhydrazine solution.

Enzyme-Linked Immunoabsorbent Assay Utilizing The Reusable Microfold TM

The immunofiltration ELISA procedure used was an indirect imminoperoxidase reaction. The phenylhydrazine treated fetal cells were loaded into the 96 well Reusable Microfold TM at $5 \times 10^4$ cells per well. The cells were immobilized by vacuum onto a glass fiber filter sandwiched in between the center and upper sections of the apparatus. The filter paper was pretreated with gelatin (3%) to prevent cross contamination of reactions between wells. The gelatin was cleared from the individual filtration channels by passing hot water through the gelatin treated filter prior to use. The cells were incubated with 50 ul of normal goat serum (NGS) for 20 min at 25° C. and the NGS was vacuumed through and away from the cells in the Reusable Microfold TM apparatus. 100 ul of hybrid cell colony supernatant was then added to each well and incubated for 60 min at RT. The cells were then vacuumed, washed in place in the apparatus six times with 250 ul of PBS with 5% CS before the addition of 100 ul of peroxidase conjugated goat anti-mouse IgG and IgM serum (affinity purified, absorbed with human serum, KPL, Inc., Gaithersburg, Md. The peroxidase conjugated antiserum was used at a 1:300 dilution in PBS with 5% CS. Following a 30 min incubation at 25° C., the cells were washed 3× with PBS+CS and 3× with Tris buffered saline, 10 mM, pH 7.4, (TBS). 100 ul of Hanker/Yates (8 mg/10 ml TBS) and 0.03% $H_2O_2$ was added to the samples and the reaction was observed for 30 min. Positive reactions consisted of the formation of a dark black-brown precipitate. The reactions were stopped with 25 ul of 4N $H_2SO_4$ and vacuumed dry in the filtration apparatus. Side by side negative and positive wells could easily be distinguished from each other. The filter paper could also be kept as a permanent record and a fresh gelatin treated filter placed in the apparatus for immediate reuse.

Solid-Phase Enzyme-Linked-Immunosorbent-Assay (ELISA)

Titration of Mc anti-EA antibody by ELISA was done as follows. 100 ul of $5 \times 10^5$ freshly harvested whole washed (5×) C57Bl/6n fetal cells fixed in 0.2% buffered glutaraldehyde with 1% BSA were added to each well of a flat-bottom polyvinyl chloride microtiter plate and incubated 2-3 hrs at 25° C. The cell suspension solution was flicked out and 100 ul of 50% NGS were added per well and the plate stored at 4° C. until used. To begin the ELISA procedure, the 50% NGS mixture was removed and 100 ul of monoclonal hybridoma supernatant diluted in PBS −1% BSA (serial 2-fold dilutions) was added to each well and the plates were incubated at RT overnight. The procedure was performed from this point as a standard indirect ELISA, with a 2 hr incubation of the peroxidase conjugate (diluted 1:500). 30 minutes following addition of chromogen, ABTS and $H_2O_2$ were added to activate the peroxidase reaction, the plates were read on a Multiscan ELISA spectrophotometer at 414 nm light wavelength. Fetal cell membranes, prepared as in Coggin, Cancer Research 39:2752 (1979); or Coggin, Methods in Cancer Research XVIII, 371-389 (1979), could also be used.

Screening Hybrid Colonies for Specificity of Antibodies to EAs

Hybridoma colony supernatants testing positive for fetal cell targets were screened for specificity by absorption of hybridoma culture supernatants with cell suspensions prepared from newborn or adult mouse tissues (C57BL/6n). Adult mouse brain, muscle, heart, liver, and kidney were collected and placed in HBSS, pH 7.4. The cells from these tissues were dispersed by pressing them through a fine wire 40 mesh screen and were washed twice in HBSS. Thirteen day fetal cells from primaparous donors were used as an EA positive control. A standard absorption curve for fetal cells was prepared using from $1 \times 10^7$ to $3 \times 10^8$ cells with 200 ul of a given Mc supernatant. The OD reading of each cell absorption sample was compared with the corresponding OD from the unabsorbed titration curve for the same Mc supernatant. The difference in the number of dilutions was calculated and the ratio of activity removed was determined by 50% removal per dilution (i.e. one dilution, 50%; 2 dilutions, 75%; 3 dilutions, 87.5%, etc.). The standard absorption was then graphed using percentage of activity removed vs. number of cells.

The specificity of Mc antibodies for fetal cells and for detecting cross reactive OFAs on tumor cells was also tested using the solid-phase (SP) ELISA. Rodent tumor cell lines dispersed non-enzymatically as target cells, were used. A fetal cell equivalent absorption value was determined for each rodent tumor cell line by comparing the percent activities removed with the corresponding percent activity removed by the same number of fetal cells. These cell types included the mouse SV40-transformed mKSA line as well as the hamster SV40-transformed WF5-1 and GD-36 lines.

RESULTS

In previous work (Coggin, J. et al., In: Ciba Foundation Symposium (ed.). Embryonic Antigens in Malignancy and Pregnancy: Common Denominators in Immune Regulation, London: Pitman Books, pp. 28–54), it was observed that polyclonal, in vivo absorbed, xenogeneic antiserum derived against 10 day gestation hamster fetal cells immunoprecipitated fetal specific polypeptides from 0.5% nonidet P-40 and 3M KCl extracts of 12–13d mouse or 10d hamster fetal cells. Several distinct fetal specific polypeptide bands in SDS-PAGE analysis were present. The derivation of Mc antibody to any of these EA determinants on the surface of hamster or mouse fetal cells was expected to be difficult as sensitization efforts were to involve immunization with syngeneic fetal cells. Pregnant, syngeneically mated female mice and hamsters might serve as a good source of EA sensitized B-cell splenocytes for hybridoma fusion but suppressor activity against anti-EA immune responses in these spleen tissues had been detected in previous studies and could restrict hybridoma development.

Syngeneically-mated, pregnant Balb/c mice were used repeatedly as a source of EA sensitized splenocytes for fusion and hybridoma production and no stable hybridomas were obtained. Further, injection of intact, irradiated, syngeneic fetal cells or soluble extracts of these cells into LSH hamsters in an effort to derive hamster: mouse P3X63Ag8.653 myeloma cell hybrids with hamster splenocytes sensitized to syngeneic fetal tissues were unsuccessful. Additionally, Balb/c mice also proved to be quite poor responders to syngeneic fetus though a few anti-EA+ reactive hybridomas were obtained using the EI assay with 12 dmfcs as target cells. Unfortunately, these hybridomas failed to passage in vitro.

Success was obtained, however, in the C57Bl/6n mouse. C57Bl/6n mice immunized with irradiated, 12 dmfcs, proved to be excellent sources of splenocytes for producing the desired anti-EA immunoglobulin-producing hybridomas. As shown in Table 2, substantial numbers of hybrid colonies producing antibody against EA+ 12 dmfcs in the EI assay were derived from the fusions of spleen cells from C57Bl/6n mice sensitized to 12 dmfcs.

the positive hybridoma colonies producing anti-EA anitbody reported in Table 2, column 4, reacted with EA+ fetal cells in a minimum of 3 separate ELISA tests with three successive uncloned hybridoma subcultures. When neonate or adult mouse cells ($10^8$/ml) were suspended in the antibody and used as absorption targets prior to testing in the EI assay on 12 dmf target cells (columns 5 and 6, Table 2), the hybridomas consistently showed no reactivity with these non-fetal tissues and antibody titers were unaffected post-absorption. However, complete absorption of the antibodies as detected in the EI assay was readily achieved with $10^6$ to $10^8$ 12 dmfcs.

TABLE 2

Initial Screening Of Hybridoma Mass Colonies On Immunofiltration ELISA Showing Positive Detection of Syngeneic EA+ 12 Day Mouse Fetal Cells (dmfc) And No Reaction With EA− 19 dmfc

| Immunization Protocol Group[a] | Total No.[b] Colonies Picked | Total No.[c] Colonies Tested | Total No.[d] Colonies Reactive (%)[e] | No. Reactive with 12 Day mfcs after Subculture No. Subcultures Tested | No. Reactive after Adsorption with Neonatal Tissues | No. Reactive after Adsorption with 12 Day Mouse/Fetal Cells |
|---|---|---|---|---|---|---|
| Short course, high fetal cell concentration | 123 | 69 | 22 (32) | 22/25 | 22/22 | 0/22 |
| Short course, low fetal cell concentration | 22 | 10 | 5 (50) | N.T.[f] | N.T. | N.T. |
| 3M KCl | 144 | 122 | 47 (38) | 11/11 | 11/11 | 0/11 |

[a]See Materials and Methods for details.
[b]Hybridoma colonies growing in HAT medium following fusion procedure.
[c]Colonies surviving transfer to 24 well plates and stabilizing to growing in HT medium.
[d]Colonies giving a minimum of 3 positive ELISA reactions with 12 d fetal cell targets. 2
[e]Reactive colonies/total no. colonies picked × 100.
[f]Not tested.

Major differences were noted in the efficacy of the various immunization protocols as reflected by the number of hybridomas obtained. Immunization with both the high dose, short term regimen of immunization with intact fetal cells and the 3M KCl extracts of 12 dmfc resulted in the highest numbers of anti-EA hybridomas giving positive ELISA reactions against syngeneic 12 dmfc in the EI screening assay. The ELISA immunofiltration (EI) assay of Glassy et al., *J. Immuno. Methods*, 58:119 (1983), permitted the detection and rapid screening of antibody to EA determinants expressed on the 12 day gestation mouse fetal cells provided adequate blocking of endogenous cellular peroxidase was performed with goat serum prior to the addition of the test hybridoma supernatant (see Methods Section for details). Adult mouse tissues and 19 day, EA− (Weppner, W. A. and Coggin, J. H., *Cancer Res.*, 40:1380 (1980)) term fetal mouse cells were non-reactive with any of the hybridoma supernatants. Care had to be exercised in selecting correct chromogen concentrations to avoid high background levels. Neither adjuvant immunization protocols with fetal cells nor long course, multiple-inoculation protocols were successful in producing suitable anti-EA hybridomas.

The survival of initial hybridoma colonies showing anti-EA antibody following subculture is also shown in Table 2. Though a total of 201 colonies (70%) survived subcultured to 24 well plastic plates and grew in the HT medium supplemented with the RAW 264.7 cell supernatants, large numbers of colonies later died out as the hybrid cells stabilized. Subsequent trials conducted in the absence of supplementation with 10% RAW supernatants indicated that the standard lymphocyte feeder cells were not effective for stabilization of the hybridomas. Results of the intial screening of tissue culture passaged hybridoma colonies for specific binding to primaparous, syngeneic EA+ 12-13 day mouse fetal cells (12 mfcs) in the EI assay are shown in Table 2. All The demonstration of the specificity of the Mc antibody derived from cloned hybridomas from these original hybridomas is described in a subsequent section. It was concluded that the short term, high dose and the 3M KCl immunization procedures were superior to all others tested. Thirty-five of the initial uncloned hybridoma cultures which passaged in tissue culture in RAW supplemented medium and which showed positive results in the EI assay using EA+ fetal cell targets were randomly selected for further study. These were subcultured and subsequently assayed for EA specificity by absorbing hybridoma supernatants with acetone powder of neonatal mouse tissue EA− or EA+ 12 dmfcs (Table 2). Positive ELISA reactions were still detected with EA+ 12 dmfc target cells following repeated adsorptions with neonatal, C57Bl/6n mouse tissues in 32 of 35 supernatant culture fluids, indicating overwhelming specificity of the anti-EA antibodies present in the uncloned culture supernatants. Removal of the anti-EA reactive immunoglobulin(s) occurred following single absorptions of the undiluted hybridoma supernatants with EA+ 12 dmfcs in 32 of 32 of the in vitro passaged, uncloned hybridomas.

Characterization and Titration of Mc Derived Against an EA Determinant

Three monoclonal antibody-producing hybridoma lines were initially obtained by cloning cells from mass colonies derived from the short term, high dose immunization procedure employing 12 dmfcs. RAW supernatant supplementation was used while achieving these cloned cells. One cloned hybridoma was obtained from the 3M KCl group and one was obtained from the short term, low dose group. Cloning of each was achieved by colony formation in methycellulose and by terminal dilution in liquid medium. Subsequent cloning using additional end point dilution and single cell isolation methods were conducted throughout the course of the study. Four Mcs were IgM isotypes and one was an IgG isotype. All 5 Mc producers have consistently yielded antibody specifically reactive with 12 dmfc's and not adult cells in the SP ELISA in many subsequent tests. Isotype switching (IgM IgG) among the 4 Mcs producing IgM was not observed even under conditions of adverse culture shock. None of the antibodies cross-reacted with fetal calf-serum or regular calf serum in gel diffusion or in the SP ELISA even when concentrated 25 fold.

Figure 1:
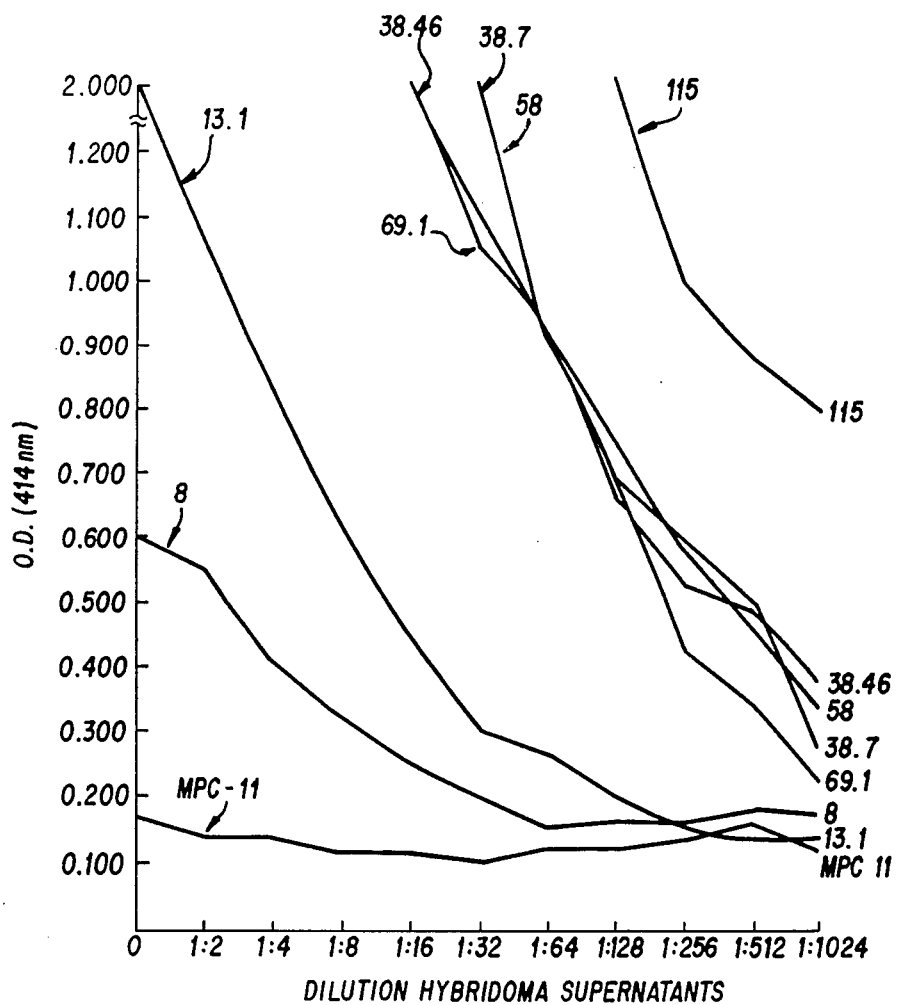
FIG. 1 shows the titration of several Mc antibodies in 10–12 day culture supernatants of the hybridomas using 12 dmfc (day gestation mouse fetal cell) targets fixed to plastic microwells in the solid phase (SP) ELISA assay. All the anti-EA monoclones shown were of the IgM isotype with the exception of Mc 58 which is an $IgG_{2a}$ isotype. MPC 11 is a control IgG Mc antibody selected from comparison because it is directed against an unknown determinant which is not a fetal related determinant (by the IE assay). MPC-11 was used as a negative control in all experiments to establish background ELISA levels in each experiment.

Using a quantitative, SP ELISA procedure performed in PVC plates, the immunoglobulins in the supernatants from the 5 hybridomas could be titered to >1024 for four of the monoclones and >2048 for the 155(sh) Mc using syngeneic 12 dmfcs as the target antigen (FIG. 1). Very similar results were obtained with several of the Mcs tested against glutaraldehyde-fixed fetal cell membranes prepared as previously described (Leffell, M. S. and Coggin, J. H., *Cancer Res.*, 37:4112 (1977) and Sijens, R. J. et al., *Hybridoma*, 2:231-234 (1983)) and used as the target antigen in the SP ELISA.

Specificity of Anti-EA Mc Antibody

Figure 2:
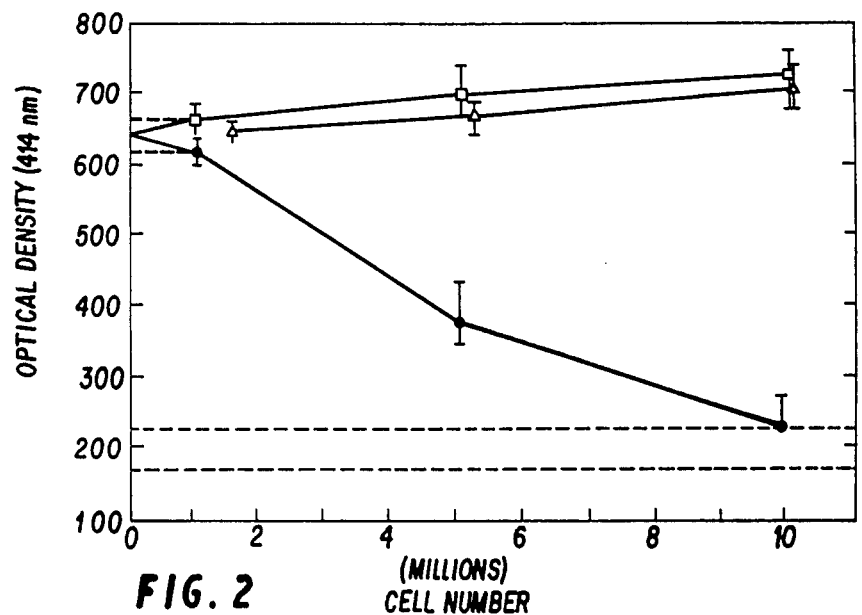
FIG. 2 demonstrates fetal specificity of another anti-EA Mc, IgM 69.1. Mc IG (650 OD units) was treated in an initial absorption with increasing concentrations of adult mouse spleen, liver, muscle, lung and skin cells (▲) or 12–13 day gestation, primaparous mouse fetal cells (●) or 24 day old, mouse muscle and spleen cells (■) for 12 hours at 4° C., centrifuged to remove the cell pellet and retitered in the solid phase ELISA assay.
Figure 4:
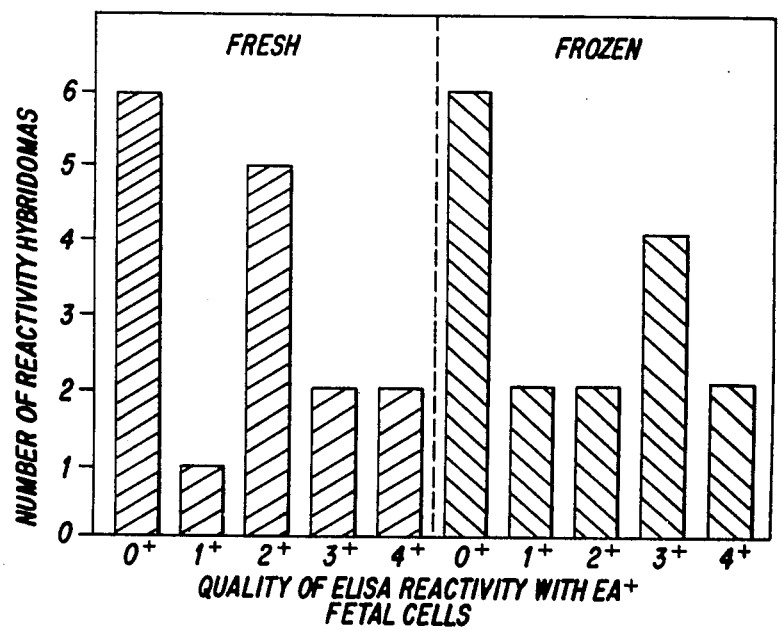
FIG. 4 shows the results of a comparison of the above supernatants in FIG. 3 for their capacity to react with 13 dmfcs which were either freshly harvested and used immediately or frozen in liquid nitrogen for one week and thawed and used in the immunofiltration ELISA assay. Both assays were performed on the same day in the same test. ELISA reactions are designated according to the rapidity of color development following addition of the chromogen (++++ =full color in 5 min.

The specificity of the 5 antibodies produced by the 5 Mc listed above was tested following absorption with either 13 dmfs or term (19d) mouse fetal cells or adult cells of the C57Bl/6n mouse. As shown in FIG. 4 for Mc 69.1, an IgM producer, a single absorption with $10^7$ 13 dmfcs but not an equal number of adult mcs removed the IgM to background levels when the absorbed supernatant was subsequently tested against EA+ 12 dmfc in the SP ELISA assay. In a second trial, twelve-day gestation fetal cells removed all the activity of Mc 69.1 with only $10^6$ cells whereas $10^8$ adult mouse cells removed no significant antibody (data not shown). Virtually identical results to those given in FIG. 2 were obtained for the 4 other Mcs when supernatant stocks (titers >1024) were diluted to give 600-800 OD units (SP ELISA) of IgM or IgG and absorbed once with $5 \times 10^6$ or $10^7$ fetal or adult mouse cells.

The absorption results for the Mc Igs obtained using EA+ cells or tissues correlated exactly with the previously detected potential of these various tissues or tumors to cross react with mouse or hamster fetal cells in tumor transplantation assays (Coggin, J. H. and Anderson, N. G., *Adv. Cancer Res.*, 19:105 (1974) and Coggin, J. H. and Ambrose, K. R., *Cancer Research*, Vol. XVIII, pp. 371-389 (Academic Press, NY) (1979)) (Table 3).

TABLE 3

Specificity of Monoclonal Antibodies to Fetal Cell Determinants[a] By Absorption Analysis

| Absorption Targets (EA Expression)[b] | Capacity of indicated tissue to remove Mc reactive with 12 dmfc in ELISA assay Monoclonal Antibody[c] | | | | |
|---|---|---|---|---|---|
| | KC158 | SL13.1 | SH115 | SH38.46 | SH69.1 |
| 13 d C57 mouse f.c. (EA+) | + | + | + | + | + |
| 10 d LVG hamster f.c. (EA+) | + | + | + | + | + |
| 10 wk human f.c. (EA+) | + | + | + | + | + |
| 17 wk human f.c. (EA+) | + | + | + | + | + |
| WF5-1 hamster cells (EA+) | + | + | + | + | + |
| mKSA mouse sarcoma cells (EA+) | + | + | + | + | + |
| GD-36 hamster lymphoma cells (EA+) | + | + | + | + | + |
| L cells (EA?) | − | − | − | − | − |
| BHK cells (EA−) | − | − | − | − | − |
| 16 d C57 mouse f.c. (EA−) | − | − | − | − | − |
| 14 d LVG hamster f.c. (EA−) | − | − | − | − | − |
| Neonate C57B1/6n cells | − | − | − | − | − |
| Adult C57 mouse cells (EA−) | − | − | − | − | − |
| Adult hamster cells (EA−) | − | − | − | − | − |
| Adult human fibroblasts (EA−) | − | − | − | − | − |
| Adult human foreskin (EA?) | − | − | − | − | − |
| Adult human peripheral blood Lymphocytes (EA?) | − | − | − | − | − |

[a]Specificity was measured by solid-phase ELISA with 12 dmfc fetal cell targets following a single absorption of the monoclonal supernatants with the indicated absorption target cells.
[b]The absorption target cells were prepared by suspending the cells by nonenzymatic methods and treating with 1% BSA in PBS. (EA+) = Cell lines known to activate T-lymphocyte mediated tumor resistance. (EA−) = Cells demonstrated not to active tumor resistance. Identical results could be obtained with acetone extracted fetal or adult tissues.
[c]Equal volumes of monoclonal supernatants and packed absorption targets were mixed and incubated with 1 h at 37° C. and 18 h at 4° C. before use in the immunofiltration ELISA on EA+ 12 dmfcs.
[d]+, indicates complete absorption of >400 OD units of antibody at 490 nm in a single absorption trial; −, ELISA reaction indicates non-absorption of 400 OD units antibody in a single absorption trial leaving >350 OD units of antibody reactivity with 12 dmfc targets; NT indicates not tested.
[e]Not tested.

The Mc antibody containing supernatants reacted strongly with xenogeneic, LVG hamster, 10 d. EA+ fetal target cells but not with adult tissues of these rodents (Table 3). Most early culture supernatants used had Mc titers of 1:512 or greater in the quantitative, SP ELISA assay. Both fresh, adult, rodent tissues and acetone-extracted adult tissues including brain, lung, heart, liver, spleen or kidney cells were tested and were unable to remove the antibodies from the various MC supernatants. The Mc antibody from each of the five cultured lines also reacted with EA+ SV40-induced or transformed WF5-1 cells, GD-36, and mKSA cells by the EI assay (Table 3), but not with long term, in vitro cultured L-cells (mouse) or contact inhibited BHK (hamster) cells.

Most interestingly, each of the antibodies were absorbed by fresh homogenates of second trimester human fetus (Table 3). Fresh or acetone powders of fresh, uncultured foreskin cells or human peripheral blood lymphocytes were not able to absorb out the Mc antibodies (Table 3).

EA Preservation by Freezing

Figure 3:
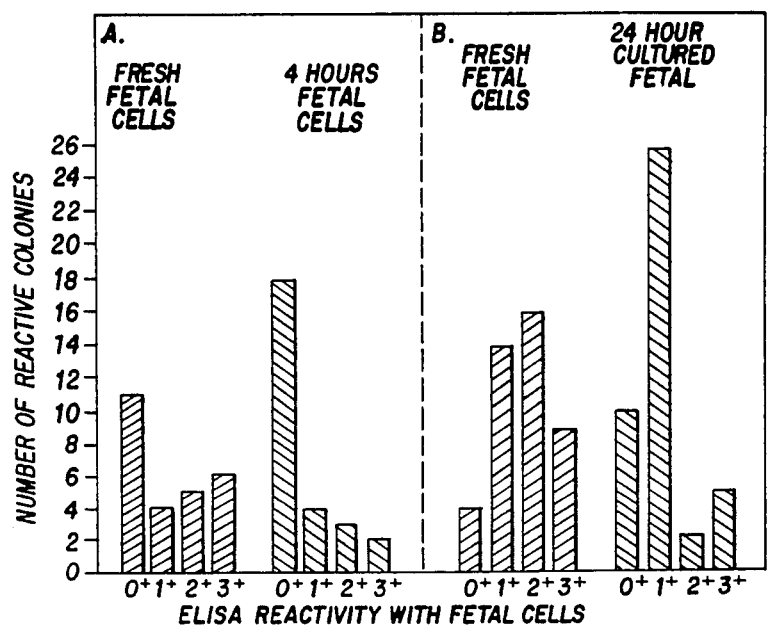
FIG. 3 shows the results of immunofiltration ELISA comparing the change in binding affinity (time to max, reactivity) of randomly selected hybridoma supernatants using target 12–13 day fetals of the mouse which were freshly harvested or cultured in vitro for 4 or 24 hours prior to testing. Cells were standardized to the same number in all cases and had the same viability (10%).

In initial screens of supernatants from uncloned hybridomas from mice sensitized to the short-course, high dose immunization protocol with 12 dmfcs, we noted that a significant shift could be detected in the reactivity patterns (FIG. 3) of a given supernatant when the freshly harvested fetal cells were compared to two fetal cells cultured for 24 hours in vitro in growth medium. Specifically, a significant shift in the degree of ELISA reactivity (No. of 2+, 3+ reactive colonies to No. of 0 or 1+ reactive colonies) was detected in many of the reactive supernatants containing IgMs from uncloned hybridomas against 12 dmfs. As shown in FIG. 4, freezing of the 13 dmfcs for 1 month at −70° C. followed by rapid thawing, preserved the same pattern and degree of ELISA reactivity of the supernatants of uncloned hybridomas in the EI ELISA assay as was observed with freshly harvested and washed 13 day mfcs.

DISCUSSION

Several reasons may account for the difficulty in obtaining stable hybridomas from mice injected more than three times with syngeneic embryo cells. Soluble, fetal cell extracts containing EA induced suppressor activity in hamsters and mice receiving multiple injections or high concentrations of crude EA+ cell extract (Coggin, J. H., In: *Ciba Foundation Symposium*, supra; Weppner, W. A. et al., *Cell Immunol.*, 54:445 (1980); Weppner, W. A. and Coggin, J. A., *Cancer Res.*, 40:1380 (1980); and Coggin, J. H. et al., *J. Natl. Cancer Inst.*, 72:853-862 (1984)). This suppressor activity was detected against lymphocytes and/or macrophages involved in tumor specific transplantation resistance directed against EA determinants on sarcoma cells. Female rodents were observed to develop cytostatic IgG to EAs cross-reactive with SV40 sarcoma cells, when immunized directly with irradiated, syngeneic fetal cells, but did not develop tumor resistance and presumably cytotoxic effector T cells under these conditions (Ambrose, K. R. et al., *J. Immunol.*, 105:524 (1970); Coggin, J. H., *Cancer Res.*, 39:2952 (1979); Irie, R. F., et al., *J. Natl. Cancer Inst.*, 63:367 (1979)).

Pregnant Balb/c mice failed to yield anti-EA producing hybridomas as did Balb/c male mice immunized with irradiated 12 dmfcs. Hamsters also failed to yield hybridomas when immunized with irradiated fetal cells. EAs present on the surface of hamster and mouse fetal cells have been difficult to characterize generally. These determinants were phase-specific for certain stages of embryo or fetal development. Fetal cells ceased to express the antigens for in vitro culture (Irie, R. F. et al., *J. Natl. Cancer Inst.*, 63:367 (1979); Hellstrom, I. et al., *Inter. J. Cancer*, 7:1:10 (1971); and Leffell, M. S. and Coggin, J. H., *Cancer Res.*, 37:4112 (1977)) with only rare exception (Ting, C. C. et al., *In Vitro*, 14:207 (1978)). Balb/c mice proved to be poor responders to syngeneic fetal sensitization as suggested by Ting et al., supra, using SV40 transformed target cells.

As reported here, male C57B1/6n mice were successfully used to derive many stable hybridomas producing antibodies to EA when immunized with syngeneic fetal cells inactivated by 5000R of x-ray. The most effective immunization protocol involved sensitization of the syngeneic host to fetal cells over a short immunization schedule.

Cloning yielded 5 stable Mcs from the first 7 hybridomas selected at random. All Mc antibodies derived against intact fetal cells were IgM producers. It was subsequently observed that all hybridomas derived by sensitization of the male mouse to the intact, irradiated, fetal cells in both short and prolonged courses yielded only IgM producers. IgG producing hybridomas could only be derived from mice receiving solubilized (3M KCl) fetal cell extracts rather than intact EA+ fetal cells. It is not known if this will remain an absolute finding for every hybridoma produced against whole fetal cells, but the results after examining several dozen different hybridoma clones to date yielded only IgM producing Mcs.

In initial trials, hybridomas made against intact fetal cells were frequently lost in the early subculture steps on feeder layers of mouse spleen cells. It was possible to obtain excellent hybridoma subculture survival and to perform efficient cloning of the hybridomas producing IGMs by supplementing the transfer medium with supernatants from the macrophage like cell line, RAW 264.7. Feeder mouse spleen cells were not useful as they have been in obtaining hybridomas to other antigens. Supplementation with RAW culture fluid has not previously been reported and was easier to do than using feeder cell layers. Apparently, the RAW 264.7 cells provide growth factor(s) required by IgM-hybridoma producing cells. The use of the filtered RAM cell supernatants also eliminated a potential source of contaminants by the addition of normal mouse spleen cells to the hybridoma cultures.

The ability to use freshly obtained, intact, mid-gestational fetal cells from primaparous mothers to screen for hybridomas producing anti-fetal Mc antibody reacting with the native EA at the cell surface was a major advantage of the Reusable Microfold TM apparatus; target cells did not have to be fixed with glutaraldehyde nor attached by centrifugation onto plates pretreated with poly-L-lysine. Cells from fresh tissues, could be processed and applied to the Reusable Microfold TM filter in minutes and a large screening of hybridoma supernatants completed in less than 3 hours. A similar method to screen human hybridomas producing IgGs to other types of cell surface antigen was recently reported by Glassy et al. (*J. Immuno. Methods*, 58:119 (1983)).

Further, the development of the SP ELISA (FIG. 1) for assaying either fixed fetal cells or fetal cell membranes made it possible to carry out quantitative absorption specificity analysis of the antibodies to EA with crude tissues. Importantly, tissues evaluated for EA or OFA expression can be analyzed without the need for in vitro culture, a definite asset in screening primary tumors or normal tissues. The SP ELISA procedure was both sensitive and highly reproducible.

The detection of evolutionarily conserved epitopes expressed on mid-gestation hamster as well as human fetus (Table 3) with the mouse Mc antibodies derived against EAs in syngeneic mouse fetus parallels the previous findings related to the immunogenicity of these fetal cell types in conferring tumor resistance, supra. No similar pattern of cross-reactivity was detected with term fetal cells or adult tissues from these species by either absorption analysis or by immunoprecipitation from adult tissues (Muller, R. et al., *Nature*, 299:640 (1982)) indicating the specificity of the Mc antibodies to true EAs embryonic-fetal specific antigen.

The observation of differential binding or absorption reactivity for SV40-induced sarcomas or lymphomas of rodents, known to be EA+, and not for mouse L cells or BHK-21 cells shows a potential tumor specific restriction or distribution of EA's detected with the 5 Mc's tested to date. Results from various studies (Coggin, J. H. et al., *J. Natl. Cancer Inst.*, 72:853-862; Rosenberg, S. A., In: *Serological Analysis of Human Cancer Antigens*, S. A. Rosenberg (Ed.) (Academic Press, New York); and Brown, J. P. et al., *J. Immunol.*, 127:539 (1981) supports the possibility of restriction of certain EAs (OFAs) to specific tumor histologic classes, although reports of common EAs on human tumors has been made by Salinas et al. (*Serological Analysis of Human Cancer Antigens,* S. A. Rosenberg (Ed.) (Academic Press, New York), pp. 539–564.), Brown et al., (*J. Immunol.,* 127:539), Jornvall et al., (*Proc. Natl. Acad. Sci.* (US), 79:287–291 (1981)) and Granatek et al. (*Science,* 224:1198–1206 (1984)). Human fetus reacted with xenogeneic polyclonal and Mc Igs to these OFAs in most reports and with the invention Mc antibodies. Several polypeptide-containing EA species immunoprecipitated by polyclonal anti-12 day mouse or 10 day hamster fetal cells, respectively, were selectively distributed among SV40 and Adv. 7-induced sarcomas. These sarcomas were known to share common OFAs which were not detected among chemically-induced sarcomas exhibiting non-cross protective immunity to SV40 sarcomas. Three polypeptide containing species of 160, 45–48 and 23 kD were found to be common to the SV40 and Adv. 7 sarcoma cells (Hellstrom, I. et al., *Inter. J. Cancer,* 7:1:10 and Weppner, W. A. et al., *Cell. Immunol.,* 54:445 (1980)).

The loss in immunogenic, as well as antigenic, activity in harvested fetus, appears to be rapid and complete for some fetal epitopes. EA+ fetal cells have been shown to lose their capacity to activate cell mediated immunity to EA+ tumors cells after only a few hours culture in vitro and were completely nonimmunogenic if not lethally irradiated prior to culture (Coggin, J. H. and Anderson, N. G., *Cancer Res.,* 40:1568 (1980) and Coggin, J. H. and Ambrose, K. R., *Methods in Cancer Research* (W. H. Fishman and H. Busch, Ed.), Vol. XVIII, pp. 371–389 (Academic Press, New York)). The results here (FIG. 3) using hybridoma supernatants and the EI assay, following culturing of target 12 day gestation mouse fetal cells for short periods (24 hours), were consistent with this previous observation.

Obtaining a constant supply of specific gestation-age fetal cells for routine analysis is important difficult because of the poor efficacy of breeding of time-mated, inbred mice. When fetal cells were available for an assay from a few, time-mated pregnant donors, they were often more plentiful than was required for a given day's experiment. The capability to freeze excess fetal cells for future use eliminates the waste of these hard-to-get and expensive cells. It was also found that the glutaraldehyde-fixed fetal cells could be successfully stored at 4° C. for a week without decreased sensitivity in the solid phase assay.

In studies reported in the following Example, the polypeptides in the fetal cells reacting with anti-EA monoclonal antibodies have been characterized. It is noted that all five of the Mc antibodies listed in Table 3 react with apparently the same polypeptide as shown by SDS-acrylamide gel electrophoresis analysis.

EXAMPLE 2

Identification of Polypeptides Reacting With Monoclonal Antibodies Prepared in Example 1

Materials and Methods

Tumor cells.

SV40 induced mouse sarcoma cells (mKsa) or hamster lymphoma cells (GD-36) were obtained from small tumor transplants in syngeneic mice or hamsters by seiving through wire mesh as described in (Payne, W. J. and Coggin, J. H., *J. Natl. Cancer Inst.* (1984)).

Human tumors were obtained as freshly frozen, primary tumors from the University of Alabama (Birmingham, Ala.) tumor bank supported by the National Cancer Institute. All tumors are histologically classed by a pathology panel and frozen in protective medium. Frozen tumor fragments were flash thawed and dispersed through wire mesh without enzyme dissociation to prepare crude cells suspensions, washed as previously described, and used for absorption studies as previously described (Payne, W. J. and Coggin, J. H., supra). Control normal tissue was obtained in many cases from histologically normal tissue adjacent to the tumor or from otherwise normal, healthy patient tissue removed with adjacent traumatized tissue for essential surgical purposes.

Monoclonal Antibodies.

Mc Igs 69.1, 38.7, 8, and 14 were derived as previously described in this disclosure against C56Bl/6n mouse fetus in syngeneic recipients. Mcs 69.1, 38.7, and 8 were IgMs and were stimulated with intact fetal cells whereas Mc 14 was induced with KCl extracts of fetal cells and was an IgG isotype. All had titers >1024 when tested against 12 dmfcs in the solid phase (SP) ELISA procedure, supra.

Isolation and Determination of Molecular Weights of EA

Fetal antigen(s) was isolated using an affinity gel column of Sepharose 4B coupled anti-mouse immunoglobulin. Two week old, high density culture supernatants of each Mc were mixed with washed, equilibrated affinity gels and incubated for 12 hrs at 4° C. The gel was washed with a 100× volume of Tris buffered saline (TBS), 10 mM, pH 7.4 and 5 ml of standard NP40 (40 ug/0.1 ml) or KCL extract (10 ug/0.1 ml) of 12 dmfcs or adult cells were mixed with the gel.

The cell extracts were prepared by treating a packed cell pellet of test tissue or cells with a 10×volume of 0.5% NP 40 in phosphate buffered saline with 1 mM PMSF. After one hr at 25° C., the cells were pelleted at 1500 rpms followed by clarification of the supernatant with 50,000×g for 30 min. The extracts and affinity gels were incubated 12–15 hrs at 4° C., then washed in the extraction buffer until no protein could be detected in the wash. KCl extracts were made as described, supra.

The antibody-antigen-Sepharose 4B complexes were then eluted with 5M $MgCl_2$ using a volume equal to the bed volume for one hr. This step was repeated again. The eluates were dialyzed with a 100×volume of TBS and used for SDS-PAGE. The eluates were treated with solubilizing buffer of 2.5% SDS, 1.25 mM urea and 1% B-mercaptoethanol in 12.5 mM Tris. The samples were then electrophoresed on a 20% to 7% (bottom to top) acrylamide gradient slab gel with Laemmli's discontinuous buffer system. Following electrophoresis, the gels were stained with Commasie blue R-250 (BioRad Labs, Inc., Richmond, VA) in acetic acid: methanol:water (7:40:53) and destained in the latter solution.

Blastogenic Activity Assessment

The lymphocyte transformation assay (LTA) was performed using splenocytes sensitized to irradiated, mKsa cells which were known to be EA positive and to undergo stimulation when subjected to KCl extracts of 12 dmfsc. KCl extracts of adult mouse cells were not stimulatory. The conditions of assay in the LTA were as reported in Weppner, W. A. and Coggin, J. H., *Cell Immunol.,* 54:193 (1980). 0.01 to 0.05 g of extract were used to achieve maximal stimulation and the calculation of the stimulation index was as described.

RESULTS

Isolation of Mc Specific Polypetide

The three IgM Mc Igs (69.1, 38.7, and 8) and the IgG Mc Ig were all observed to selectively bind a 44–48 kD polypeptide as well as a larger 200 kD polypeptide multimer. The 46 kD protein was only detected in the fetal cell extract and was not present in extracts of adult mouse tissues including muscle, skin, liver, spleen, heart, intestine, brain, or in whole animal homogenates of 19–21 day fetus of the C57BL/6n mouse. This result was true even when the adult extracts were used at 25 times the concentration present in fetal extracts of 12–13 dmfcs.

Other bands present in the eluates from the affinity gels were: light chain+J chain of IgM from the added monoclonal antibody (20–23 kD), heavy chain from the IgG in the sandwich affinity gel used to bind mouse Mc IgM (57 kD), serium albumin (70 kD) and Igm heavy chain (75 kD), along with a fetal specific 200 kD polypeptide which may represent a multimer of the 46 kD EA protein monomer. The antibody fragments from the affinity gel were present in both lanes representing adult as well as fetal affinity gels as was expected. Importantly, the specificity of affinity gel binding of the 46 and 200 kD polypeptide for added EA specific Mc Igs was demonstrated by using a nonrelevant mouse Mc IgM known to be specific for Moloney sarcoma virus envelope glycoprotein (MSV). This unrelated Mc Ig did not bind either of the epitope bearing polypeptides detected with the Mcs listed above.

A 25×concentrate of Mc 69.1 was prepared and used to absorb a KCl extract of 12 mdfsc (500 ug protein) using the affinity gel above. The extract was recovered from the gel with the bound EA removed by the Mc IgM and concentrated to its original volume. A sample was re-evaluated by SDS-PAGE analysis and compared to the original KCl extract. The results showed that all detectable 46 and 200 kD bands were removed.

This affinity absorbed extract was then tested in the LTA to determine if the removal of the 46 kD polypeptide (or its multimer) prevented stimulation of EA-sensitized mouse splenocytes prepared as described in Weppner, W. A. and Coggin, J. H., *Cell Immunol.*, 54:193 (1980). The results in Table 4 showed that indeed the IgM absorbed extract failed to stimulate the EA-sensitized lymphocytes whereas the unabsorbed KCl extract was stimulatory.

TABLE 4

KCl Extract of 12 dmfcs Treated Before and After Treatment with the Sepharose 4B:69.1 Mc IgM Antibody Affinity Gel

| Extract Treatment | Stimulation Index in Lymphocyte Transformation Assay |
|---|---|
| Untreated 12 dmfc eluate (46 kD and 200 kD polypeptides present) | 27 ± 5 |
| 69.1 treated 12 dmfcs eluate (46 and 200 kD polypeptide not present) | 6 ± 3 |

46 kD Protein in Human Tumors

As shown in Table 5, a spectrum of human tumors including carcinomas of the lung, breast, colon, and rectum were observed to selectively absorb several of the Mcs above when subsequently assayed in the SP ELISA assay on 12 mfcs. Adult control tissues and normal tissues from several of the patients whose tumors were included as well were negative for absorption of the same Mcs. Affinity gel analysis of the KCl extract of two lung adenocarcinomas revealed a significant 46 kD band and a trace of the 200 kD band in both tumors and the absence of these polypeptides in equal protein concentrations of normal adult tissues.

TABLE 5

Absorption of Anti-Fetal Monoclonal Antibodies with Human Tumors and Control, Normal Tissues as Determined in the Solid Phase ELISA[1]

| Monoclone No. | Tumor | | No. Cells Used | Absorption Ratio[2] | 12 mfc Equivalency[3] |
|---|---|---|---|---|---|
| 69.1 | Adenocarcinoma of colon | 61-70 | $6 \times 10^7$ | 0.44 | 0.24 |
| 69.1 | Adenocarcinoma of colon | 52-26 | $7 \times 10^7$ | 0.58 | 0.28 |
| 38.46 | Adenocarcinoma of colon | 62-19 | $6 \times 10^7$ | 0.53 | 0.29 |
| 38.46 | Adenocarcinoma of colon | 61-70 | $4.1 \times 10^7$ | 0.50 | 0.40 |
| 38.46 | Adenocarcinoma of colon | 56.26 | $10^8$ | 0.57 | 0.18 |
| 69.1 | Adenocarcinoma of colon | HT12 | $5 \times 10^7$ | 0.64 | 0.42 |
| 69.1 | Adenocarcinoma of colon | 57-62 | $7 \times 10^6$ | 0.28 | 1.32 |
| 69.1 | Lung carcinoma | 64-71 | $1.2 \times 10^8$ | 0.48 | 0.13 |
| 69.1 | Lung carcinoma | 64-56 | $1.5 \times 10^8$ | 0.03 | 0 |
| 69.1 | Lung carcinoma | HS-47 | $1.2 \times 10^7$ | 0.34 | 1.06 |
| 69.1 | Gastric carcinoma | HT-18 | $5 \times 10^7$ | 0.75 | 2.03 |
| 69.1 | Gastric carcinoma | 64-29 | $1.98 \times 10^8$ | 0.50 | 0.12 |
| 38.46 | Gastric carcinoma | 64-29 | $10^8$ | 0.51 | 0.23 |
| 38.46 | Gastric carcinoma | HT-23 | $1.93 \times 10^8$ | 0.40 | 0.15 |
| 69.1 | Gastric carcinoma | HT-28 | $8 \times 10^7$ | 0.33 | 0.33 |
| 69.1 | Carcinoma larynx | 59-91 | $1.1 \times 10^8$ | 0.14 | 0 |
| 69.1 | Carcinoma | 62-31 | $2.3 \times 10^7$ | 0.31 | 2.3 |

TABLE 5-continued

Absorption of Anti-Fetal Monoclonal Antibodies with Human Tumors and Control, Normal Tissues as Determined in the Solid Phase ELISA[1]

| Monoclone No. | Tumor | No. Cells Used | Absorption Ratio[2] | 12 mfc Equivalency[3] |
|---|---|---|---|---|
| 69.1 | Carcinoma larynx | 56-61 | $4.5 \times 10^7$ | 0.46 | 2.9 |
| 69.1 | Carcinoma larynx | 56-12 | $2.4 \times 10^8$ | 0.70 | 0.10 |
| 69.1 | Adenocarcinoma larynx | 56-12 | $3.6 \times 10^8$ | 0.65 | 0.18 |
| 38.46 | Adenocarcinoma breast | HT-14 | $6.5 \times 10^7$ | 0.25 | 0.78 |
| 69.1 | Adenocarcinoma breast | SH-27 | $8.2 \times 10^7$ | 0.34 | 0.73 |
| 69.1 | Adenocarcinoma breast | SH-37 | $8.9 \times 10^7$ | 0.39 | 0.69 |
| 38.46 | Rectal carcinoma | HT-11 | $1.76 \times 10^8$ | 0.03 | 0 |
| 69.1 | Rectal carcinoma | HT-11 | $1.76 \times 10^8$ | 0.68 | 0.08 |
| 69.1 | Normal adult mouse | | $3 \times 10^8$ | 0 | 0 |
| 69.1 | Normal adult mouse | | $3 \times 10^8$ | 0 | 0 |
| 69.1 | Normal adult mouse | | $3 \times 10^8$ | 0 | 0 |
| 38.46 | Normal adult mouse | | $3 \times 10^8$ | 0.05 | 0.01 |
| 38.46 | Normal adult mouse | | $3 \times 10^8$ | 0.15 | 0.06 |
| 38.46 | Normal adult mouse | | $3 \times 10^8$ | 0.12 | 0.04 |

[1]Standardized McIg of each type listed were absorbed for 12 hrs. with the indicated number of tumor cells or normal control tissue admixtures (spleen, heart, muscle, colon, lung and liver) and reasssayed in the solid phase ELISA using EA+ 12 day gestation mouse fetal cells.

[2]Absorption ratio = $\frac{\text{O.D. (414 nm) absorbed Ig}}{\text{O.D. (414 nm) unabsorbed}}$ ; 0 = no absorption; 1.0 = complete absorption.

[3]Determined by comparing absorption ratio (AR) of test tumor or normal target cells with AR of 12 dmfcs for the same McIg. (e.g., $\frac{1.8 \times 10^4 \text{ test target cells} = 1 \text{ O.D. unit}}{3.3 \times 10^4 \text{ 12 dmfcs} = 1 \text{ O.D. absorption unit}}$ (from standard absorption curve) = 0.54.

DISCUSSION

These results identify common 46 and 200 kD polypeptides in mouse fetal cells reactive with several anti-EA specific Mc Igs that could not be detected in extracts of adult mouse cells or term fetal cells of mice or men. The proteins were also detected in a spectrum of human carcinomas but could not be detected in normal human tissues examined including colon, spleen, brain, skin and muscle. The presence of a 200 kD, fetal-specific polypeptide bound in Sepharose 4B affinity gel by all of the Mc Igs suggested that the epitopes for the Mc Igs might reside in a multimer of the 46 kD protein in its native form in fetal cells and tumor cells.

The finding that fetal and tumor cells of mouse and man share evolutionary conserved 46 and 200 kD polypeptides was most revealing. The additional finding that selective removal of the polypeptides by affinity chromatography using the Mc IgM rendered the extract non-stimulatory to lymphocytes sensitized to EA or tumor and fetal cells is also interesting. This observation clearly suggests that these peptides may contain at least one of the EA determinants responsible for the induction of cross-protective tumor transplantation resistance induced by fetal cells or their extracts in syngeneic mouse and hamster.

Five hybridomas selected in this disclosure for random specific further studies were deposited for 30 years at the ATCC, Rockville, Md., prior to the filing date. The accession numbers are:

Hybridoma 8 (also denoted as 8 KCL III): ATCC No. HB-8663;

Hybridoma 69.1 (also denoted as 69.1 sh III): ATCC No. HB-8664;

Hybridoma 38.46 (also denoted as 38.46 sh III): ATCC No. HB-8665;

Hybridoma 38.7 (also denoted as 38.7 sh III): ATCC No. HB-8666; and

Hybridoma 115 (also denoted as 115 sh III): ATCC No. HB-8667.

What is claimed as new and is intended to be covered by Letters Patent of the United States is:

1. A process of preparing a hybridoma secreting on-cofetal-specific monoclonal antibodies, which comprises:
   (a) immunizing an animal with immunizing amounts of a non-proliferating syngeneic mid-gestation fetal cell preparation;
   (b) isolating immunized lymphocytes from said animal; and
   (c) fusing said lymphocytes under appropriate fusion conditions with an immortalizing cell line to thereby obtain said hybridoma.

2. The process of claim 1 wherein said hybridoma is cultured in the presence of the RAW 264.7 mouse macrophage cell line.

3. The process of claim 1 wherein said animal being immunized is a rodent.

4. The process of claim 1 wherein said monoclonal antibodies secreted by said cell lines are specific to rodent and human embryo and fetal cells and to rodent and human tumor cells.

5. The hybridoma prepared by the process of claim 1.

6. A process of preparing a monoclonal antibody having specificity to a given animal tumor which comprises:
   preparing a hybridoma secreting said monoclonal antibody by the process of claim 1; and
   obtaining said monoclonal antibody from said hybridoma.

7. The process of claim 6 which comprises screening for said monoclonal antibody, among those antibodies which show substantially no affinity for normal adult animal tissue.

8. A monoclonal antibody prepared by the method of any of claims 6 or 7.

9. A monoclonal antibody having the following specificity characteristics:
   (a) immune reactivity towards rodent mid-gestation antigens;
   (b) immune reactivity towards human oncofetal tumor antigens;
   (c) substantially no immune reactivity towards rodent late gestational fetal tissue; and
   (d) substantially no immune reactivity towards human normal tissue.

10. The monoclonal antibody of claim 9 which has immune reactivity toward an oncofetal polypeptide of approximate molecular weight 44,000 to 48,000.

11. The antibody of claim 9 in detectably labelled form.

12. The antibody of claim 9 in insolubilized form.

13. The antibody of claim 9 which is of mouse origin.

14. The antibody of claim 9 which is IgM.

15. A method of detecting an oncofetal antigen associated with a human tumor which comprises:
   incubating a human specimen suspected of containing said oncofetal antigen with the monoclonal antibody of claim 9; and
   determining if any substantial binding occurs between said antigen and said antibody.

16. The method of claim 15 which comprises an immunometric assay.

17. The method of claim 5 which comprises an enzyme-linked assay.

18. The method of claim 15 which comprises a radioimmunoassay.

19. The method of claim 15 which comprises a competitive immunoassay.

20. The method of claim 15 wherein the determination of substantial binding between said antigen and said antibody is carried out in the presence of detectably labelled oncofetal antigen.

21. The method of claim 15 wherein said antigen comprises the polypeptide having a molecular weight of about 44,000 to 48,000.

22. The method of claim 15 wherein said antigen comprises a polypeptide having a molecular weight of about 200,000.

23. A molecular complex comprising the monoclonal antibody of claim 9 bound to antigen, wherein said antigen comprises a polypeptide having a molecular weight of 44,000–48,000 or a polypeptide having a molecular weight of 200,000.

24. The complex of claim 23, wherein said antigen is present on or associated with human tumor cells.

25. The complex of claim 24 wherein said antigen is present on or associated with human tumor cells in vivo.

26. The complex of claim 23, wherein said antibody is detectably labelled.

27. The complex of claim 26 wherein said label is selected from the group consisting of an enzyme, a radioisotope, a fluorescent label, and a metal label.

28. The complex of claim 23 wherein said monoclonal antibody is of mouse origin.

29. The complex of claim 23 which is present in an in vitro system.

30. The complex of claim 23 wherein said monoclonal antibody is substantially free of antibodies having substantially different specificity.

31. The complex of claim 23 wherein said antibody is IgM.

32. A method of imaging an animal tumor which comprises contacting said tumor with the monoclonal antibody of claim 11 and
   detecting the presence of said antibody on or associated with said tumor.

33. The method of claim 32 wherein said antibody is labelled with a radiolabel or a metal label.

34. A method of suppressing the growth of tumor cells which comprises administering to said cells a tumor growth suppressing amount of a monoclonal antibody according to claim 9, bound to a tumor growth-suppressing substance.

35. A hybridoma cell line producing a monoclonal antibody having the following specificity characteristics:
   (a) immune reactivity towards rodent mid-gestation antigens;
   (b) immune reactivity towards human onco-fetal tumor antigens;
   (c) substantially no immune reactivity towards rodent late gestational fetal tissue; and
   (d) substantially no immune reactivity towards human normal tissue.

36. The hybridoma cell line of claim 35 wherein said monoclonal antibody has immune reactivity toward an onco-fetal polypeptide of approximate molecular weight 44,000 to 48,000.

37. The hybridoma cell line of claim 35 or 36 which is the product of a fusion between a mouse lymphocyte and a mouse myeloma cell line.

38. The hybridoma cell line of claim 37 in which said monoclonal antibody is IgM.

39. The hybridoma cell line of claim 35 having the identifying characteristics of ATCC No. HB-8663, HB-8664, HB-8665, HB-8666, or HB-8667.

* * * * *